United States Patent [19]

Corey et al.

[11] Patent Number: 4,657,855

[45] Date of Patent: Apr. 14, 1987

[54] COMPOSITION AND TEST DEVICE FOR DETERMINING THE PRESENCE OF LEUKOCYTES, ESTERASE AND PROTEASE IN A TEST SAMPLE

[75] Inventors: Paul F. Corey; A. Christopher Skjold, both of Elkhart; James H. Pendergrass, South Bend; Lonnie Stover, Elkhart, all of Ind.

[73] Assignee: Miles Laboratories, Inc., Elkhart, Ind.

[21] Appl. No.: 597,338

[22] Filed: Apr. 6, 1984

[51] Int. Cl.4 .......................... C12Q 1/44; C12Q 1/38
[52] U.S. Cl. ........................................ 435/19; 435/23; 435/34; 435/805; 422/56
[58] Field of Search ................. 549/65, 479; 548/541, 548/556; 435/19, 23; 424/3; 436/903

[56] References Cited

U.S. PATENT DOCUMENTS 4,278,763  7/1981  Berger et al. .......................... 435/23
4,299,917  11/1981  Berger et al. .......................... 435/23
4,551,428  11/1985  Berger et al. .......................... 435/19

Primary Examiner—Sidney Marantz
Assistant Examiner—David A. Saunders
Attorney, Agent, or Firm—Roger N. Coe

[57] ABSTRACT

A composition for determining the presence of leukocytes, esterase or protease in a test sample. The composition comprises an ester having the structure

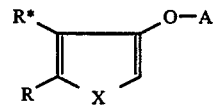

in which: A is an N-blocked-amino acid residue or an N-blocked-peptide residue, X is O, S or NR', R is aryl, or lower alkyl, R* is H, or lower alkyl, and R' is H, lower alkyl or aryl; and a suitable buffer substance.

33 Claims, No Drawings

COMPOSITION AND TEST DEVICE FOR DETERMINING THE PRESENCE OF LEUKOCYTES, ESTERASE AND PROTEASE IN A TEST SAMPLE

CONTENTS

1. Introduction
2. Background of the Invention
   2.1 Chromogenic Esters
   2.2 Accelerators
   2.3 Diazonium Salt Coupling Agents
   2.4 Summary
3. Summary of the Invention
4. Definitions
   4.1 N-blocked-amino acids and peptides
   4.2 Aryl
   4.3 Lower Alkyl
   4.4 Suitable Buffer Substance
   4.5 Accelerator
   4.6 Fused Ring Systems
5. The Composition
   5.1 The Ester
   5.2 The Buffer
   5.3 The Accelerator
   5.4 The Diazonium Salt
6. The Test Device
7. Experimental
   7.1 General Information
   7.2 Preparation of the Ester
      7.2.1 Synthesis of 3-(N-tosyl-L-alaninyloxy)-5-phenylpyrrole
      7.2.2 Synthesis of 3-(N-tosyl-L-alaninyloxy)-5-phenylthiophene
      7.2.3 Synthesis of 3-(N-tosyl-L-alaninyloxy)-1-methyl-5-phenylpyrrole
      7.2.4 Synthesis of 3-(N-tosyl-L-alaninyloxy)-5-(p-chlorophenyl)pyrrole
   7.3 Preparation and Use of Various Test Devices
      7.3.1 Test Device in which the ester is 3-(N-tosyl-L-alaninyloxy)-5-phenylpyrrole
      7.3.2 Test device in which the ester is 3-(N-tosyl-L-alaninyloxy)-5-phenylthiophene
      7.3.3 Test device in which the ester is 3-(N-tosyl-L-alaninyloxy)-1-methyl-5-phenylpyrrole
      7.3.4 Test Device in which the ester is 3-(N-tosyl-L-alaninyloxy)-5-(p-chlorophenyl)pyrrole
   7.4 Evaluation of the Test Device

1. INTRODUCTION

The present invention relates to a novel composition and test device useful in assaying a test sample for the presence of analytes such as leukocyte cells, esterase and protease. The invention is particularly useful in detecting leukocyte levels in body fluids such as urine, and reduces the laboratory procedure for such assay from a cumbersome counting procedure requiring microscopic observation, to a rapid, facile dip-and-read operation.

The presence of an abnormally high level of leukocytes in a patient's urine is possibly indicative of such pathological conditions as kidney or urogenital tract infection or other dysfunction. Accordingly, accurate urinary leukocyte information can be an invaluable tool to the physician in diagnosis and treatment of such pathologies.

Traditionally, the medical profession has relied on visual determination techniques to count leukocyte population in urine sediment or uncentrifuged urine, a process requiring expensive equipment such as a centrifuge and microscope, as well as inordinate time expenditure on the part of the clinician. Moreover, the traditional techniques suffer from the disadvantage that only intact cells are determined. Leukocytes occurring in the urinary system are subject to conditions which can favor extensive cell lysis. For example, it is known that in urines of abnormally high pH, leukocyte half life can be as low as 60 minutes. Since lysed cells escape detection in visual examination techniques, erroneously low determinations and false negatives can result.

Of the two techniques of microscopic leukocyte analysis'urine sediment and non-centrifuged, homogenized urine—the former is clearly the most desirable. Although dependable results can inure to the latter, urine sediment observation is used in an overwhelming majority of instances. It requires that the urine sample be centrifuged and the sediment isolated and subjected to microscopic inspection. The analyst then counts the number of leukocytes appearing in the viewing field. This task is further complicated by the presence of other urinary components in the sediment such as epithelial cells and salt particles. The varying content of sediment constituents, coupled with other complicating factors including non-homogeneity of the sample and differing optical powers among microscope equipment, can lead to enormous errors in the ultimate determination.

It is thus apparent that a quick, facile method of leukocyte determination, one which would eliminate the need for time-consuming techniques, as well as cost-consuming equipment, and which would provide accurate responses to esterase, protease or leukocyte cells, whether the cells are intact or lysed, would indeed constitute a quantum advance in the state-of-the-art. The present invention provides such an advance. Moreover, it is based, not on the ability to *see* leukocytes, but on the enzymatic activity they exhibit, and therefore is substantially free of the inaccuracies described above.

2. BACKGROUND OF THE INVENTION

Prior to the present invention, methods for determining hydrolytic analytes included chromogenic esters which, when hydrolyzed by esterase or protease, produced a colored alcoholic product, the intact ester being of a different color from the free alcohol. Many of these systems included accelerator compounds and diazonium salt coupling agents.

2.1 Chromogenic Esters

Thus, there exists in the prior art a body of references which disclose the use of certain esters which, when cleaved by enzymatic activity, result in the formation of color or other detectable species. British Pat. No. 1,128,371 discloses the use of indoxyl and thioindoxyl esters as useful chromogens in detecting hydrolytic enzymes in body fluids. The enzymes cleave the ester to generate free indoxyl, which subsequently oxidizes to form the dimeric product indigo, a readily observable blue dye. Such activity is said to be due to, among other enzymes, cholinesterase. This patent also teaches that, in addition to the indoxyl portion of the ester substrate, the acid radical is chosen with particular reference to the enzyme to be detected. For example, it is stated that the acid radical can be acetate, laurate or stearate for detection of esterase or lipase, respectively. For detecting enzymes such as phosphatase or sulfatase the acyl radical can be inorganic. Thus, the British Patent teaches the use of chromogenic esters as substrates for determining esterolytic enzymes, such esters comprising indoxyl or thioindoxyl as the alcoholic moiety of the ester, the acyl moiety being tailored to the particular enzyme to be determined.

The affect of careful acyl radical selection is nowhere more clearly exemplified than in two references which demonstrate esterase specificity for esters in which the acyl radical comprises an N-protected amino acid or peptide. Thus Janoff, et al., *Proc. Soc. Exper. Biol. Med.* 136: 1045-1049 (1971) teaches that alanine esters are specific substrates for esterase obtained from human leukocytes. Specifically, this reference teaches that an extract of human leukocyte granules is capable of hydrolyzing n-acetyl-L-alanyl-L-alanyl-L-alanine methyl ester. Moreover, L-alanine-p-nitrophenyl ester was similarly hydrolyzed to yield the yellow p-nitrophenol colorform.

Similarly, Sweetman et al., *Jour. Hist. Soc.*, 22:327-339 teaches the use of 1-naphthyl N-acetyl-DL-alanine, 1-naphthyl N-acetyl-L-alanyl-L-alanyl-L-alanine and 1-naphthyl butyrate to demonstrate the presence of esterase.

U.S. Pat. No. 4,278,763, assigned to Boehringer Mannheim GmbH, combines these teachings in arriving at the indoxyl or thioindoxyl esters of amino acids or peptides as still another example of a traditional colorogenic substrate for leukocytic esterase activity. Like the Janoff and Sweetman references, the Boehringer patent teaches the equivalence of protease and esterase in their esterolytic penchants.

2.2 Accelerators

It is known that ester hydrolysis reactions can be activated by the presence of many nucleophilic agents, including a myriad of alcohols. Thus, the rate of hydrolysis of phenyl acetate and p-nitrophenyl acetate by esterase is increased 2.5 to 5.5 times upon addition of methanol or butanol. Greenzaid and Jencks, *Biochemistry*, 10(7), 1210-1222 (1971). Moreover, the effect increases with the length of the n-alkyl group. Wynne and Shalatin, *Eur. J. Biochem.*, 31: 554-560 (1972).

In particular, this activation affect of alcohols has been observed with esters of amino acids. p-Nitrophenyl-N-acetyl-L-alaninate hydrolysis is activated (accelerated) by the presence of methanol. Fastrez and Fersht, *Biochemistry*, 12(11), 2025-2034 (1973). High molecular weight alcohols increase the rate of esterase-induced hydrolysis of p-nitrophenyl-t-BOC-L-tyrosinate. Ashe and Zimmer, *Biochem. and Biophys. Res. Comm.*, 75(1), 194-199 (1977). The disclosure of U.S. Pat. No. 4,299,917 describes other known ester hydrolysis activators such as certain metal complexes, pyridine derivatives and imidazoles.

2.3 Diazonium Salt Coupling Agents

Also known is the use of certain diazonium salts to couple with phenols and pseudophenols to produce azo dyes. Martinet and Dornier *Compt. Rend.*, 170, 592 (1920). Such a technique is used in an esterase analysis whereby indoxyl esters are hydrolyzed via esterase to produce indoxyl, which is in turn coupled with a diazonium salt to form the corresponding azo dye. Holt and Hicks, *J. Cell Biol.* 29, 261-366 (1966); Gossrau, *Histochemistry*, 57, 323-342 (1978); West German Offenlegungschrift No. 30 17 721, filed May 9, 1980.

2.4 Summary

To summarize the background of technological developments leading up to the present invention, several methods are known for assaying hydrolytic enzymes and leukocyte cells in solution. For measuring leukocyte populatons, in urine, for example, microscopy has long been the preferred method. Thus, the technician was required to make a microscope slide of a urine sample and count the number of leukocyte cells in the field of view of a microscope; a procedure requiring an inordinate expenditure of time and expensive equipment such as a microscope and centrifuge.

Chemical and biochemical techniques are rapidly challenging the microscope for assaying leukocytes in diagnostics and are time-honored tools in the research laboratory. Chromogenic esters which have formed the keystone of chemical tests include the following alcoholic and acyl moieties:

| Alcoholic (phenolic) Moieties | Acyl Groups |
| --- | --- |
| indoxyl | acetate |
| thioindoxyl | butyrate |
| p-nitrophenyl | laurate |
| α-naphthol | stearate |
|  | amino acid |
|  | peptide |

Chemistries utilizing such esters have been abetted by various hydrolysis accelerators, as well as diazonium salt coupling agents. As accelerators, many alkanols have been employed, as have certain metal complexes, pyridine derivatives and imidazoles. Diazonium cations having appropriate anions ionically bound or associated therewith are well known as coupling agents for such chemistries, whereby the alcohol (phenol) formed upon hydrolysis of the ester is coupled with the diazonium salt for forming an azo dye.

3. SUMMARY OF THE INVENTION

The present invention provides a new test composition and device for determining the presence of leukocytes, esterase or protease in a test sample. The composition comprises an ester having the structure

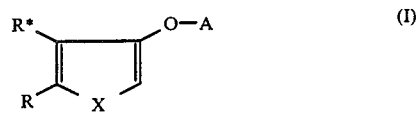

in which: A is an N-blocked-amino acid residue or an N-blocked-peptide acid residue; X is O, S, or NR'; R is aryl, or lower alkyl; R* is H, or lower alkyl; and R' is H, lower alkyl or aryl. In addition, the composition includes a suitable buffer substance. The composition can also include an accelerator (such as an alkanol having 1-15 carbon atoms), and/or a diazonium salt coupling agent.

The test device comprises a carrier matrix incorporated with the ester and buffer, and can additionally include the accelerator and/or coupling agent.

The method for using the composition or device comprises contacting a test sample suspected of containing leukocyte cells, esterase or protease with the composition or test device, and observing a detectable response.

4. DEFINITIONS

Certain terms used in the present discussion should at this point be mentioned to assure that the reader is aware of their respective meanings. Thus, the following definitions are provided to clarify the scope of the present invention, and to enable its formulation and use.

4.1 The expressions "N-blocked-amino acid residue" and "N-blocked-peptide residue" require definition on two counts. "N-blocked" refers to the chemistry of the amine group of an amino acid or peptide whereby a hydrogen bound to the nitrogen atom is replaced by a protective group such as acetyl, p-toluenesulfonyl (tosyl), tert-butyloxycarbonyl (t-BOC) and other N-protective groups known in the art.

By the terms "amino acid residue" and "peptide residue" is meant an amino acid or peptide molecule without the —OH of its carboxyl group.

4.2 By the expression "aryl" is meant any ring system containing aromaticity. Included by the term are such 5- and 6-membered rings as pyrrole, phenyl, and pyridyl, as well as fused ring systems such as naphthyl. Thus, the aromatic ring system can be heterocyclic or homocyclic, and can be substituted or unsubstituted, provided the substituent groups(s) not interfere with ability of the composition to hydrolyze in the presence of leukocyte cells, esterase or protease. Selection of such substituents is a routine laboratory determination, given the present disclosure.

4.3 The expression "lower alkyl", as used in the present disclosure, is an alkyl moiety containing about 1–6 carbon atoms. Included in the meaning of lower alkyl are methyl, ethyl, n-propyl, isopropyl, n-butyl, sec-butyl, tert-butyl and all isomers of pentyl and hexyl. These can be unsubstituted, or they can be substituted provided they not interfere with the ability to the composition or test device to detect leukocyte cells, esterase or protease.

4.4 By "suitable buffer substance" is meant a buffer which, when contacted with an aqueous test sample, will provide a resultant pH of at least about 7. Preferably the buffer is one capable of producing a pH in the range of about 7–10 and, optimally, 8.5–9.0. Boric Acid-NaOH, Bicine(N,N-bis[2-hydroxyethyl]-glycine, or CHES(2-[N-cyclohexylamino]ethanesulfonic acid) are exemplary of suitable buffer substances.

4.5 The expression "accelerator" relates to any compound which serves to increase the rate of hydrolysis of the chromogenic esters described herein. Included are such chemically diverse substances as pyridine, imidazole and their derivatives; metal complexes of the formula $D_m[B(CN)_n(NO)_p]$ in which D is alkali metal, B is a heavy metal ion, P is 0 or 1, m is 2–5, n is 4–8, and m is the sum of n and the valence of B; and alcohols. Suitable alcohols have from 1 to about 15 carbon atoms. Linear alcohols are preferred over branched chain alcohols, although the latter are included within the scope of the invention.

4.6 By "fused ring system" is meant two or more aromatic rings that share a pair of carbon atoms. For example, in the structure

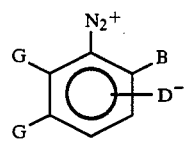

(II)

both of G can together form the fused ring system

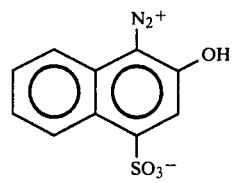

(III)

in which both of G together constitute $-(CH)_4-$. Yet another example is

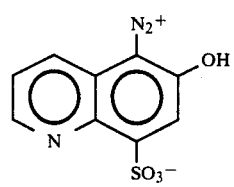

(IV)

in which both of G together constitute $-(CH=CH-CH=N)-$. Hence, the fused ring system is polynuclear, aromatic, and can be heterocyclic or homocyclic.

4.7 The expression "detectable response" is intended herein as meaning a change in or occurrence of a parameter in a test means system which is capable of being perceived, either by direct observation or instrumentally; and which is a function of the presence of a specific analyte in an aqueous test sample. Some detectable responses are the change in or appearance of color, fluorescence, reflectance, pH, chemiluminescence and infrared spectra.

5. THE COMPOSITION

The composition of the present invention includes an ester and a buffer. While there is great latitude in choosing these ingredients, there are preferred embodiments of each which produce maximized results, i.e., a high degree of detectable response developing in a short time. This optimization can be still further promoted by including an accelerator and/or a diazonium salt in the composition.

5.1 The Ester

Both the composition and test device of the present invention include an ester of the formula I and a suitable buffer. The preferred ester is one in which X is NR' and the preferred R' substituent is H. Another preferred embodiment is where the acyl moiety, A, is a N-blocked-amino acid residue in particular N-blocked-L-alaninate. It is especially preferred to use as the ester the compound

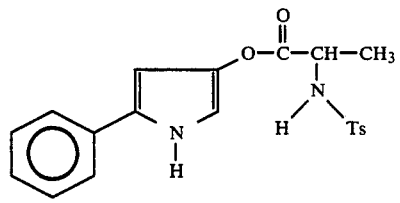

(V)

where Ts is p-toluenesulfonyl, i.e., compound I in which A is N-Ts-L-alaninate, R* is H, R is phenyl, and X is NH.

5.2 The Buffer

As is stated, supra, the buffer substance includes a multitude of compounds. The preferred pH range to be produced by the buffer is about 7–10, with 8.5–9.0 being the optimum pH range. To achieve this optimum pH range, it is presently preferred to use Boric acid-NaOH, Bicine (N,N-bis[2-hydroxyethyl]glycine), or CHES(2-[N-cyclohexylamino]ethanesulfonic acid) as the buffer.

5.3 The Accelerator

The composition of the present invention can include, in addition to the ester and buffer, various accelerators such as are defined in paragraph 4.5. Alcohols have been found to be especially useful in increasing esterase and protease catalyzed hydrolysis of the esters discussed herein. Alcohols having 8–15 carbon atoms are preferred for this purpose, while decanol, undecanol and dodecanol are preferred for use volatility as compared with alcohols of lower molecular weight.

5.4 The Diazonium Salt

The composition can also include a diazonium salt as a coupling agent. Participation of the diazonium salt in the overall reaction scheme can be represented as follows:

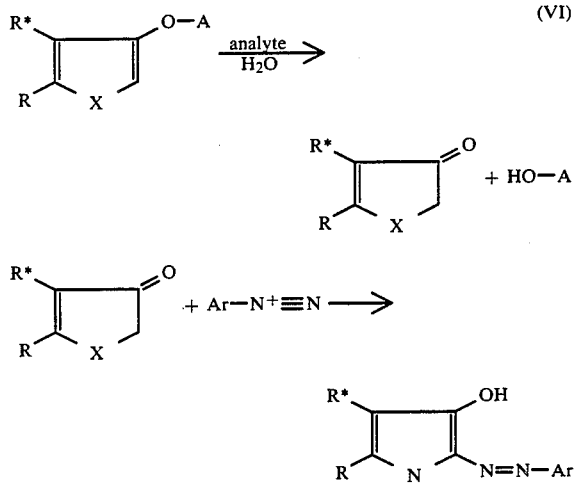

in which $ArN^+ \equiv N$ is the diazonium salt, and A, R, R* and X are as defined supra. The reaction product VI is an azo dye which can exhibit a deep, distinctive color.

The salt $ArN^+ \equiv N$ can take on a plethora of meanings. Generally it is an aromatic diazonium salt, and has as its generic structure the following:

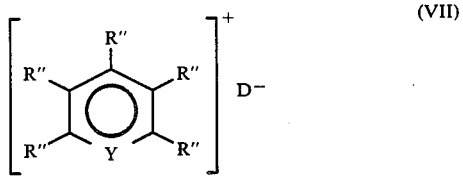

in which R″, same or different, is H, lower alkyl or aryl, or in which two adjacent R″ together form a fused ring system, with the proviso that one of R″ is $-N^+ \equiv N$, i.e., diazonium. Y is N or CR″. $D^-$ is an anion such as chloride, bromide, or other appropriate counterion to the diazonium moiety.

A diazonium salt which is self-contained, i.e., a zwitterion, serves as an excellent coupling agent. Such compounds have the structure

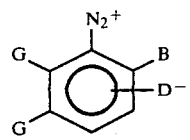

in which B is H, lower alkyl or OH; $D^-$ is a covalently bound anion; G, same or different, is H, lower alkyl or aryl, or in which both of G together form a fused ring system.

Thus the zwitterion is a species of diazonium salt wherein the counterion to the diazonium group is covalently bound to the ring system. Examples of such anions include sulfonyl ($SO_3^-$), carbonyl ($CO_2^-$), phosphonyl ($PO_3^-$), and others. It has been found most advantageous to use 1-diazo-2-naphthol-4-sulfonate.

6. THE TEST DEVICE

The composition described above can be used by itself in determining leukocytes, esterase or protease, or it can be incorporated with a carrier matrix to form a test device, thereby providing a tool for rapid, reliable estimation of the presence of the analyte. The carrier matrix is usually, but not necessarily, a porous substance such as filter paper. Other art-recognized forms of carrier matrix materials are felt, porous ceramic strips, and woven or matted glass fibers (U.S. Pat. No. 3,846,247). Also suggested are the use of wood, cloth, sponge material and argillaceous substances (U.S. Pat. No. 3,552,928). Alternatively, the carrier matrix can be nonporous, such as various polymeric films, glass and the like. All such carrier matrix materials are feasible for use in the present invention, as are others. It has been found that filter paper is especially suitable.

In a preferred method of preparing the device a piece of filter paper is wetted with an aqueous solution of the buffer. This first-dip solution can also contain various processing excipients such as a detergent, a sizing agent such as polyvinylpyrrolidone, and other inert ingredients.

The impregnated filter paper is then dried and wetted with a second-dip solution, in acetone or other nonaqueous solvent, containing the ester and, if desired, the accelerator and/or diazonium salt. The twice-impregnated paper is then dried a second time, thus forming a test device sensitive to the presence of leukocytes or other analytes.

The dried, reagent-bearing carrier matrix can be mounted on a backing material if desired. In a preferred embodiment of the test device, a filter paper carrier matrix is incorporated with the composition as described, supra, the matrix being affixed to one side to an elongated piece of transparent polystyrene film. The matrix is secured to the film by any suitable means, such as double faced adhesive tape (Double Stick ® available from 3M Company), the other end of the polystyrene film serving as a handle. In use, such a device is held by the free end of the polystyrene film backing material and the matrix end is immersed into the test sample (e.g., urine) and quickly removed. Any color formation or other detectable response is observed after a predetermined time and compared with a reference standard corresponding to responses to known concentrations of leukocytes or other analyte having esterase or protease activity. It has been found that an incubation time of about 1–3 minutes is usually sufficient to enable color development to occur in the reagent-containing filter paper.

7. EXPERIMENTAL

The following examples are provided to further assist the reader in making and using the present invention. Thus, preferred embodiments are described in experimental detail and analyzed as to the results. The examples are meant to be illustrative only, and are in no way intended as limiting the scope of the invention described and claimed herein.

7.1 General Information

In the following experimental discussion abbreviations are used as indicated:

g = gram
kg = kilogram
L = liter
mL = milliliter
M = molar
mM = millimolar
N = normal
eq = equivalents
mol = gram molecular formula (moles)
mmol = gram molecular formula $\times 10^{-3}$ (millimoles)
aq = aqueous
hr = hour
TLC = thin layer chromatography Infrared (IR) spectra were obtained with a Perkin-Elmer Model 710B or 237 infrared spectrophotometer as solutions in CHCl$_3$ unless otherwise noted; the 1602 cm$^{-1}$ band of polystyrene film was used as an external calibration standard. Signals are reported as cm$^{-1}$.

Proton magnetic resonance ($^1$H NMR) spectra were obtained at 89.55 MHz using a JEOL FX-900 spectrometer or at 60 MHz using a Varian T-60 spectrometer; spectra were obtained in CDCl$_3$ solution unless otherwise noted. Chemical shifts are reported in part per million downfield from the internal standard tetramethylsilane.

Carbon-13 magnetic resonance ($^{13}$C NMR) spectra were obtained at 22.5 MHz using a JEOL FX90Q spectrometer with Fourier transform and with full proton broad-band noise decoupling; spectra were obtained in CDCl$_3$ solution unless otherwise noted. Carbon shifts are reported in parts per million downfield from the internal standard tetramethylsilane.

Mass spectra (MS) were obtained on a Hewlett-Packard 5985A spectrometer operating in either an electron impact (EI) or a fast atom bombardment (FAB) mode. High-resolution mass spectra were obtained on an AEI MS-902 spectrometer.

Organic reagents were obtained from Aldrich Chemical Company and were used without purification, unless otherwise noted. Inorganic reagents were ACS reagent grade from Fisher Scientific Company or other major vendor. Reaction solvents were ACS reagent grade; tetrahydrofuran (THF) was HPLC grade from J. T. Baker Chemical Company. Brine refers to a saturated aqueous sodium chloride solution.

Thin layer chromatography (TLC) was performed using silica gel 60F-254 plates from E. Merck. Column chromatography was performed using E. Merck Silica Gel 60 (70–230 mesh). All melting points and boiling points reported are uncorrected.

7.2 Preparation of the Ester

The following experiments were performed to illustrate the synthesis of the ester of the present invention. While these experiments relate to specific starting materials and end products, it is believed that the procedures are applicable to a broad range of species included within the generic class of esters disclosed herein.

7.2.1 Synthesis of 3-(N-tosyl-L-alaninyloxy)-5-phenylpyrrole (4)

The synthesis of 3-(N-tosyl-L-alaninyloxy)-5-phenylpyrrole is illustrated in the following reaction sequence:

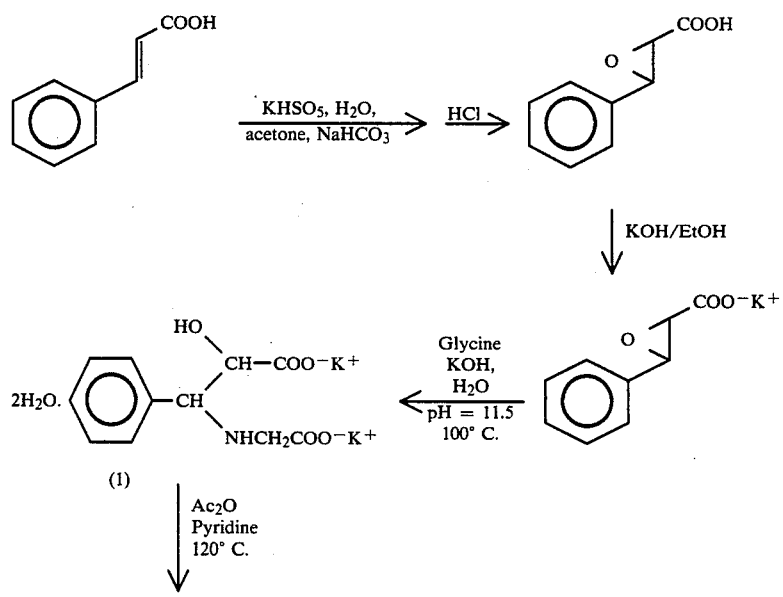

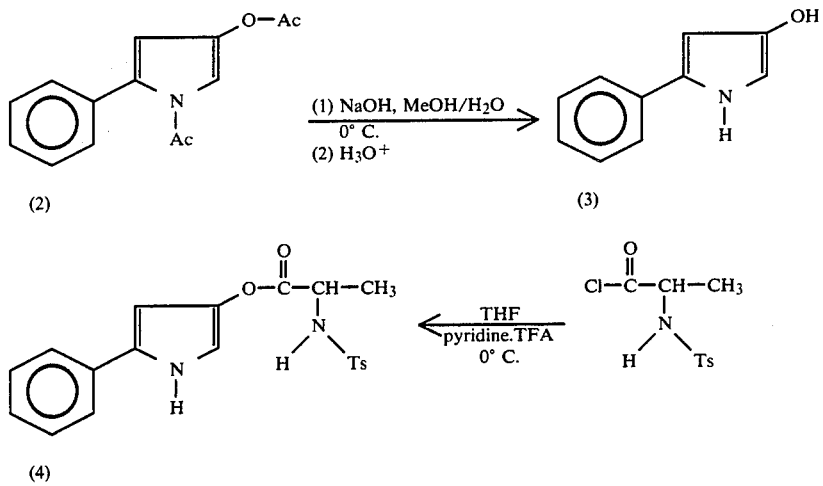

N-tosyl-L-alanine

L-alanine (100 g; 1.11 moles) was dissolved in 2.25 L of 1N sodium hydroxide (aq), cooled to 5° C. and stirred while a solution of p-toluenesulfonyl chloride (218 g; 1.11 moles) dissolved in 450 mL of toluene was added slowly. The mixture was stirred at ambient temperature for 20 hr. The layers were separated and the chilled aqueous layer acidified to pH 1 with concentrated hydrochloric acid. The white solid title compound was collected by filtration, washed with water and dried. Yield 178.5 g (66%) mp 134°-5° C. IR (CHCl$_3$) cm$^{-1}$ 1726, 1340, 1165, 1095; $^1$H NMR (DMSO-D$_6$) δ 1.20 (d, J=7, 3H), 2.40 (s, 3H), 3.85 (p, J=8, 1H), 6.4 (br s, 1H)(CO$_2$), 7.41 (d, $|J_{AB}|$=8, 2H) and 7.75 (d, $|J_{AB}|$=8, 2H) [center of pattern: 7.58; $\Delta V_{AB}$=20.49 Hz], 8.03 (br d, J=8, 1H)(NH).

N-tosyl-L-alaninyl chloride

Method A

A mixture of N-tosyl-L-alanine (12.4 g; 0.05 mol) and thionyl chloride (25 mL) was heated for 90 minutes at 55° C., and then concentrated on the rotary evaporator at 40° C. The red solid residue was dissolved in 200 mL of boiling CCl$_4$, decolorized with 20 g of oven-dried Norit® 211 (American Norit Co., Inc.), filtered and chilled. The cream colored solid title product was collected by filtration, washed with hexane and dried. Yield 8.48 g (65%) with mp 101°-101.5° C. IR (CHCl$_3$) cm$^{-1}$ 3360, 3260, 3025, 1775, 1605, 1350, 1170, 910; $^1$H NMR (CDCl$_3$) δ 1.48 (d, J=7, 3H), 2.43 (s, 3H), 4.33 (p, J=8, 1H), 5.93 (br d, J=8, 1H)(NH), 7.31 (d, $|J_{AB}|$=8, 2H) and 7.76 (d, $|J_{AB}|$8, 2H) [center of pattern: 7.53; $\Delta V_{AB}$=26.83 Hz].

Anal. calcd. for C$_{10}$H$_{12}$ClNO$_3$S: C, 45.89; H, 4.62; N, 5.35; Found: C, 46.63; H, 4.90; N, 5.19.

Method B

A mixture of N-tosyl-L-alanine (3.1 g; 13 mmol) and thionyl chloride (6 mL) was heated for 90 min at 50° C., then diluted with 50 mL of dry hexane. The mixture was stirred rapidly, chilled and the solid product filtered. Yield 3.15 g (93%) mp 99°-100° C. The IR spectrum was identical to that of the recrystallized material prepared by Method A.

2-Hydroxy-3-(carboxymethylamino)-hydrocinnamic acid Dipotassium salt dihydrate (1)

A stirred slurry of 1.0 kg of trans-cinnamic acid (6.75 mol) in 4.5 L acetone was treated first with NaHCO$_3$ (2.47 kg; 29.4 mol; 4.36 eq) then carefully with water (4.5 L). The resulting thick mixture was treated dropwise, over 1.5-2.0 hr, with a solution of OXONE ® (Dupont Co.) monosulfate compound (3.78 kg; contains 1.825 eq of KHSO$_5$) in 0.4 mM aqueous disodium ethylenediamine tetraacetic acid (EDTA) (14.5 L; prepared by dissolving 2.17 g disodium EDTA dihydrate in 14.5 L distilled water).[1,2] During this addition the reaction temperature was maintained at 24°-27° C. using a water bath; the reaction pH was noted to be about 7.4. After the addition was completed the mixture was stirred an additional 0.5 hour then cooled to about 10° C. The reaction was acidified with conc. HCl (~1.2 L) to pH=2 while maintaining the temperature at around 10° C., and then treated with CH$_2$Cl$_2$ (5.05 L) and stirred vigorously for 10 minutes.

1. J. O. Edwards, et al, *Photochem. Photobiol.* 30, 63 (1979). 2. R. Corci, et al, *J. Org. Chem.* 45, 4758 (1980).

After allowing the mixture to settle, the aqueous layer was decanted off and the organic layer, which contained insoluble salts, was filtered through paper with suction. The filtered solids were washed with CH$_2$Cl$_2$ (1.9 L) and the aqueous layer extracted with this filtrate. The filtered solids were again washed with CH$_2$Cl$_2$ (3.15 L) and the aqueous layer extracted with this filtrate. The combined CH$_2$Cl$_2$ layers were extracted with a solution of KOH (593.3 g) in water (6.31 L)—gentle heating to about 40° C. is often required to dissolve a solid which may separate during the base extraction. The CH$_2$Cl$_2$ layer was then extracted with a solution of KOH (99 g) in water (1.5 L) and the combined base extracts treated with glycine (481.7 g; 6.416 mol; 0.95 eq); the organic layer was discarded.

The solution pH was adjusted to 11.5 with 25% aqueous KOH then heated to boiling. Approximately 900 mL of low boiling liquid (acetone and water) was distilled off until the vapor temperature reached 99° C., following which, the mixture was refluxed for 2 hours. After cooling, the reaction mixture was extracted with CH$_2$Cl$_2$ (3.15 L), the CH$_2$Cl$_2$ phase discarded and the aqueous phase evaporated to dryness under reduced pressure with a 70° C. bath. The residue was boiled in 95% EtOH (8.83 L) for 30 minutes, then allowed to cool slowly with stirring, whereupon the product separates as fine crystals. These were filtered, washed with fresh 95% EtOH (1.26 L) and dried in a 50°-60° C. oven to give the title compound (1.77 kg; 74.6%) as white crystals with mp=120°-2° C. (uncorrected).

IR (KBr) cm$^{-1}$ 3420 (br.), 1590 (br.), 1410, 1130, 710; $^1$H NMR (D$_2$O-TSP) δ 3.1 (s, 2H), 3.89 (d, $|J_{AB}|=4$, 1H) and 4.52 (d, $|J_{AB}|=4$, 1H) (center of pattern: 4.21; $\Delta V_{AB}=18.83$ Hz.), 4.68 (s, 6H, exchangable protons), 7.4 (s, 5H); TLC Rf=0.59 (EtOH:1M triethylammonium bicarbonate, 7:3)

Anal. Calcd. for C$_{11}$H$_{15}$NO$_7$K$_2$: C, 37.59; H, 4.30; N, 3.99; Found: C, 37.22; H, 4.24; N, 3.96.

N-acetyl-3-acetoxy-5-phenylpyrrole (2)

A suspension of 2-hydroxy-3-(carboxymethylamino)-hydrocinnamic acid dipotassium salt dihydrate (1) (1.0 kg; 2.84 mol) in pyridine (3.0 L) was treated with acetic anhydride (4.0 L) at ambient temperature under an inert gas atmosphere. A mild exothermic reaction ensued and the reaction temperature rose exponentially to 60°-70° C. during a period of 1.5-2.5 hours. Once the reaction began to cool the mixture was heated to 120°-123° C. for 15 minutes, then allowed to cool to ambient temperature over 1 hour, during which time pyridinium acetate separated as crystals. The mixture was filtered through paper with suction and the salts washed with EtOAc until colorless; the filtrate was evaporated to dryness in vacuo.

The dark red residue was dissolved in EtOAc (3.0 L) washed three time with water (1.0 L) each), dried over MgSO$_4$ and treated with Darco ®-G60 (ICI Americas, Inc.) (300 g). After stirring for 30 minutes the mixture was filtered through Celite ® (Johns-Manville) and evaporated to dryness in vacuo to give a reddish-orange oil. This oil was dissolved in warm 2-propanol (1.2 L), then allowed to cool slowly to ambient temperature overnight, whereupon a solid separated. The crystalline product was filtered, washed with 50% aqueous 2-propanol and dried in vacuo to give the title compound (417 g; 60%) with mp=58°-60° C. (uncorrected). A portion was taken up in Et$_2$O, treated with Norit 211, filtered and concentrated under reduced pressure; on standing at 0° C. colorless tiny needles separated. These were filtered, washed with Et$_2$O/Hexane (1:1) and vacuum dried to give the analytical sample with mp=60°-62.5° C. (uncorrected).

IR (CHCl$_3$) cm$^{-1}$ 3020, 1760, 1730, 1595, 1378, 1320, 1220 (br.), 1030, 960, 903; $^1$H NMR (CDCl$_3$) δ 2.23 (s, 3H), 2.27 (s, 3H), 6.18 (d, J=2, 1H), 7.35 (s, 5H), 7.42 (d, J=2, 1H); TLC Rf=0.56 (toluene:dioxane, 4:1).

Anal. Calcd. for C$_{14}$H$_{13}$NO$_3$: C, 69.12; H, 5.38; N, 5.76; Found: C, 68.88; H, 5.25; N, 5.53.

3-Hydroxy-5-phenylpyrrole (3)

A finely divided portion of N-acetyl-3-acetoxy-5-phenylpyrrole (2) (36.8 g; 0.15 mol) was freed of oxygen by stirring in a flowing argon stream for 10 minutes, then suspended in deoxygenated MeOH (379 mL), cooled to −6° C. (in a −15° C. methanol (MeOH)/dry-ice bath) under an inert gas atmosphere and rapidly treated with an ice cold deoxygenated solution of 2N NaOH (300 mL). The reaction temperature rose immediately upon addition of base to 18° C., and after ~3 minutes the reaction mixture became homogeneous. As the reaction mixture cooled, compound (3) separated as fine crystals. After 15 minutes a solution of cold deoxygenated 2M citric acid (150 mL) was added, the resulting mixture was stirred for 10 minutes, and then filtered. The solid was washed thoroughly with deoxygenated water (200 mL), taking care to minimize exposure of the product to air, then dried under vacuum overnight to yield the title compound (22.3 g; 93.6%) as light pink tiny needles.

IR (KBr) cm$^{-1}$ 3400, 3110, 2900, 1600, 1580, 1555, 1480, 1268, 1180, 742, 640; $^1$H NMR (DMSO-D$^6$) δ 6.1 (m, 1H), 6.3 (m, 1H), 7.0-7.7 (m, 5H), 8.0 (s, 1H), 10.4 (br s, 1H); TLC Rf=0.20-0.28 (EtOH:CHCl$_3$, 1:9).

Anal. Calcd. for C$_{10}$H$_9$NO: C, 75.45; H, 5.70; N, 8.80; Found: C, 75.30; H, 5.69; N, 8.67.

3-(N-tosyl-L-alaninyloxy)-5-phenylpyrrole (4)

A solution of anhydrous tetrahydrofuran (THF, 450 mL), pyridine (43.8 mL; 0.542 mol; 1.2 eq) and trifluoroacetic acid (85.0 mL; 1.10 mol; 2.4 eq), maintained at 0° C. under an inert gas atmosphere, was treated in one portion with 3-hydroxy-5-phenylpyrrole (3) (71.5 g; 0.45 mol; 1.0 eq) followed immediately by the dropwise addition, over 5-10 minutes of a solution of freshly prepared N-toysl-L-alaninyl chloride (141.0 g; 0.54 mol; 1.2 eq) in anhydrous THF (450 mL). The resulting mixture was stirred for 15 minutes at 0° C. The reaction was then quenched by addition of a solution of 1.0M aqueous citric acid (315 mL) and EtOAc (1.35 L). After brief mixing the phases were separated and the organic layer washed with a solution of aqueous NaCl (360 mL; 0.18 g NaCl per mL of water). The organic layer was next extracted twice with a solution of 5% aqueous NaHCO$_3$ (1.35 L each), and then washed with another portion of aqueous NaCl (360 mL; 0.18 g NaCl per mL of water). The reddish brown organic layer was stirred at ambient temperature for 15 minutes with MgSO$_4$ (101 g) and Darco-G60 (143 g), then filtered through Celite and evaporated to dryness in vacuo from a 37° C. bath to give (4) as a pinkish-white solid. The crude product was ground to a powder and dissolved in warm (50° C.) THF (250 mL), stirred vigorously and diluted with n-hexane (250 mL). The stirring was continued for 1 hour at ambient temperature as the product crystallized. The solid was filtered, washed with toluene (ca. 1.0 L) until the filtrate was colorless, then dried in vacuo overnight to yield the title compound (112 g; 65%) as a white powder with mp=154.5°-155° C.).

IR (KCl) cm$^{-1}$ 3350, 3325, 1760, 1508, 1320, 1155, 770; $^1$H NMR (DMSO-d$^6$) δ 1.33 (d, J=7, 3H), 2.36 (s, 3H), 4.13 (p, J=8, 1H), 6.25 (m, 1H), 6.73 (m, 1H), 7.05-7.50 (m, 5H), 7.5-7.85 (m, 4H), 8.42 (d, J=8, 1H), 11.18 (br s, 1H); $^{13}$C NMR (DMSO-d$^6$) ppm 18.335, 21.001, 51.370, 98.061, 108.336, 123.423, 126.024, 126.610, 128.560, 128.756, 129.601, 132.397, 137.600, 138.380, 142.737, 169.919; [α]$_D$=−70° (c=1.11, MeOH); TLC Rf=0.45 (EtOAc:hexane, 1:1); TLC Rf=0.40 (toluene:dioxane, 4:1).

Anal. Calcd. for C$_{20}$H$_{20}$N$_2$O$_4$S: C, 62.48; H, 5.24; N, 7.29; Found: C, 62.62; H, 5.27; N, 7.30.

7.2.2 Synthesis of 3-(N-tosylalaninyloxy)-5-phenylthiophene (9)

A series of experiments was conducted to prepare 3-hydroxy-5-phenylthiophene by minor modifications of the reported literature procedures[3,4] outlined on a following page. The resultant hydroxythiophene was then acylated with N-tosyl-L-alaninyl chloride to give the corresponding N-tosyl-L-alaninate ester in 46% yield (unoptimized procedure).

3. P. Friedlander and S. Kielbasinski, *Chem. Ber.* 45, 3389 (1912). 4. A. I. Kosak, R. J. F. Palchak, W. A. Steele and C. M. Selwitz, *J. Amer. Chem. Soc.* 76, 4450 (1954).

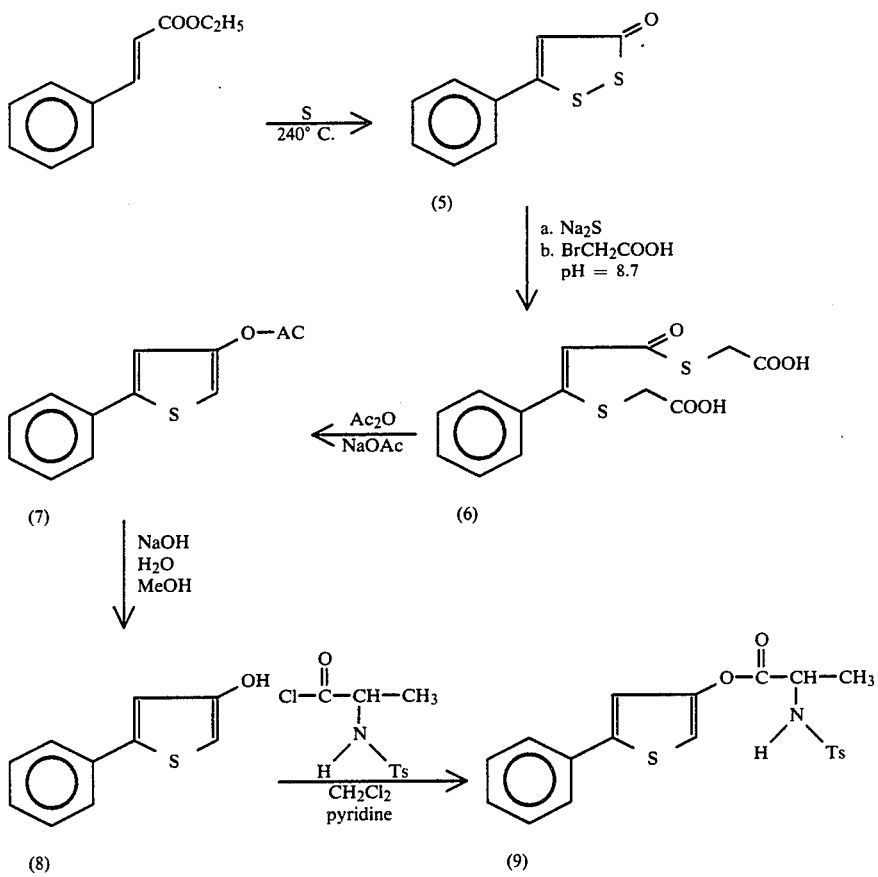

3-Phenyl-1,2-dithia-3-cyclopenten-5-one (5)

A suspension of 10 g of ethyl cinnamate (56.82 mmol) and 10 g of sulfur was heated at 250° C. for four hours in a 50 mL flask equipped with a distillation head and receiver to remove ethanol produced during the reaction. The reaction mixture was then allowed to cool to 100° C. and added to 500 mL of refluxing ethanol. The resulting precipitate was filtered and successively triturated with 500 mL of boiling acetone and twice with 500 mL portions of ethanol. The combined supernatants were concentrated to a black solid, which was crystallized from methanol to give dark brown needles. A second recrystallization from methanol using Norit and filtration through Celite gave 2.023 g of light yellow needles mp 113°–115° C.

IR (KBr) cm$^{-1}$ 1650, 1550, 1390, 1350, 1130, 770; $^1$H NMR (60 m Hz, CDCl$_3$) $\delta$6.92 (s, 1H), 7.58 (m, 5H); TLC Rf=0.5 (dichloromethane).

Anal. Calcd. for C$_9$H$_6$O$_2$S: C, 55.64; H, 3.11; Found: C, 55.53; H, 3.47.

cis-4-Keto-6-phenyl-3,7-dithia-5-nonenedioic acid (6)

A molten solution of 35.48 g of sodium sulfide nonahydrate (148 mmol) at 94° C. was treated with 6.65 g of 3-phenyl-1,2-dithia-3-cyclopenten-3-one (5) (34.23 mmol) added portionwise over five minutes. After fifteen minutes, the mixture was added to an ice-cold solution containing 43.6 g of bromoacetic acid (314 mmol) in 60 mL of H$_2$O containing to pH 8.7 with sodium carbonate. The resulting solution was maintained at 0° C., pH 8.7 for 45 minutes, and was then filtered. The supernatent was maintained at 0° C. and acidified to pH 3.7 with a 5N HCl solution. The resulting mixture was stirred overnight at 5° C. The supernatant was then decanted, and the resulting oil triturated with ether. The oil was evaporated with toluene until 6.98 g of a colorless foam was obtained (65%). This material was used without further purification.

An analytical sample was obtained from the ether supernatant, which upon concentration, successive evaporation with acetic acid and toluene, and trituration with ether, gave tan crystals. mp=142.5°–150° C.

IR(KBr) cm$^{-1}$ 1705, 1655; $^1$H NMR (60 MHz, DMSO-D$_6$) $\delta$2.06 (s, CH$_3$CO$_2$H impurity) 3.30 (s, 2H), 3.77 (s, 2H), 5.67 (m, 2H) (OH), 6.37 (s, 1H), 7.43 (m, 5H); TLC Rf=0.85 (chloroform:methanol:acetic acid, 5:5:1).

Anal. Calcd. for C$_{13}$H$_{12}$S$_2$O$_5$: C, 50.00; H, 3.88; Found: C, 50.26; H, 3.98.

3-Hydroxy-5-phenylthiophene Acetate (7)

A vigorously stirred suspension of 3.40 g of crude cis-4-keto-6-phenyl-3,7-dithia-5-nonenedioic acid (6) (10.9 mmol), 3.40 g of sodium acetate (41.5 mmol), and 30 mL of acetic anhydride was heated to reflux for one hour. The mixture was allowed to cool and was then filtered and evaporated to give a black oil. This residue was dissolved in 75 mL of ethyl acetate and extracted three times with 50 mL portions of ice-cold saturated sodium bicarbonate solution. The organic layer was then washed with brine, dried over sodium sulfate, filtered, and evaporated to give 2.826 g of a black solid.

The crude product was purified by evaporative distillation at 120°–140° C. and 0.1 mm to give 1.235 g of a light orange oil which solidified upon standing (52%).

IR cm$^{-1}$ 1700, 1745; $^1$H NMR (60 MHz, CDCl$_3$) δ2.23 (S, 3H), 7.03 (d, J=2 Hz, 1H), 7.13 (d, J=2 Hz, 1H); 7.23–7.73 (m, 5H); MS (EI, DIP) m/e 218 (M$^+$, 12.6%); TLC Rf=0.48 (hexane:ethyl acetate, 5:1).

Anal. Calc. for C$_{12}$H$_{10}$SO$_2$.½H$_2$O: C, 63.41; H, 4.88; Found: C, 63.78; H, 4.86.

3-Hydroxy-5-phenylthiophene (8)

A mixture of 2.126 g of 3-hydroxy-5-phenylthiophene acetate (7) (9.74 mmol) and 80 mL of methanol under an argon atmosphere was treated with 11 mL of 1N NaOH. After 20 minutes, the reaction was quenched by the addition of 11 mL of 1N HCL, evaporated at 25° C., 12 mm, to approximately 50 mL volume, and treated with 100 mL of ethyl acetate. The organic layer was separated, washed with brine, dried over sodium sulfate, filtered, and evaporated to give a black solid. This residue was dissolved in 75 mL of ethyl acetate and dried over MgSO$_4$. Filtration and evaporation gave a black solid which was triturated four times with hot hexane to give upon cooling a total of 837 mg of a yellow solid, mp 74°–75° C. (49%). The combined mother liquors were concentrated to give 0.87 g of a solid which was chromatographed over 100 g of SiO$_2$ eluted with a hexane:ethyl acetate (7:1) solvent mixture. Obtained after recrystallization was an additional 380 mg of product. mp 73.5°–74° C. The combined yield was thus 1.217 g (71%). mp 74.5°–75° C. (Lit[3,4] 75° C., 78° C.).

IR cm$^{-1}$ 3880, 1635; $^1$H NMR (90 MHz, CDCl$_3$) δ3.81 (s, 2H), 6.57 (s, 1H), 7.2–7.7 (m, 5H); MS (EI) m/e 176.0 (70.7%); TLC Rf=0.23 (hexane:ethyl acetate, 1:5).

Anal. Calcd. for C$_{10}$H$_8$OS: C, 68.15; H, 4.57; Found: C, 68.05; H, 4.70.

3-(N-tosyl-L-alaninyloxy)-5-phenylthiophene (9)

A solution containing 440 mg of 3-hydroxy-5-phenylthiophene (8) (2.5 mmol) in 20 ml of dichloromethane and 0.61 mL of pyridine (7.5 mmol) at 0° C. under an argon atmosphere was treated with a solution containing 1.314 g of N-tosyl-L-alaninyl chloride (5 mmol) in 10 mL of dichloromethane added dropwise over a period of five minutes. The reaction was allowed to stir for 0.5 hour at 0° C., and was then poured into 100 mL of chloroform. The mixture was then successively extracted with 50 mL portions of 1N citric acid, water, ice-cold sodium bicarbonate solution, water, and brine. The mixture was then dried over sodium sulfate, filtered, and evaporated to give 1.78 g of a brown oil. Attempted crystallization from toluene after treatment with 1.78 g of Norit was unsuccessful. The residue was then chromatographed on a 200 g column of SiO$_2$ eluted with dichloromethane at a flow rate of 10 mL/minute. Fractions containing the product were pooled and concentrated to give 951 mg of a reddish oil. The product was crystallized from toluene. Successive recrystallization from toluene gave a total of 463 mg of product as light yellow solid, (46%). mp 85°–87° C.

IR (KCl) cm$^{-1}$ 1735, 1330, 1150; $^1$H NMR (90 MHZ, CDCl$_3$) δ1.53 (d, J=7 Hz, 3H), 1.62 (s, 3H), 4.23 (m, 1H), 5.32 (d, J=9 Hz, 1H), 6.84 (d, J=1.4 Hz, 1H), 6.88 (d, J=1.4 Hz, 1H), 7.23–7.83 (m, 9H); MS (FAB) m/e 402 (M+1, 15%); TLC Rf=0.20 (hexane-ethyl acetate, 4:1).

Anal. Calcd. for C$_{20}$H$_{19}$NO$_4$S: C, 59.83; H, 4.77; N, 3.59; Found: C, 59.60; H, 4.77; N, 3.43.

7.2.3 Synthesis of 3-(N-tosyl-L-alaninyloxy)-1-methyl-5-phenylpyrrole (13)

A series of experiments was conducted to prepare the captioned ester corresponding to compound (I) in which A is N-tosyl-L-alaninyl, R is phenyl, R* is H, X is NR' and R' is CH$_3$. The reaction sequence is as follows:

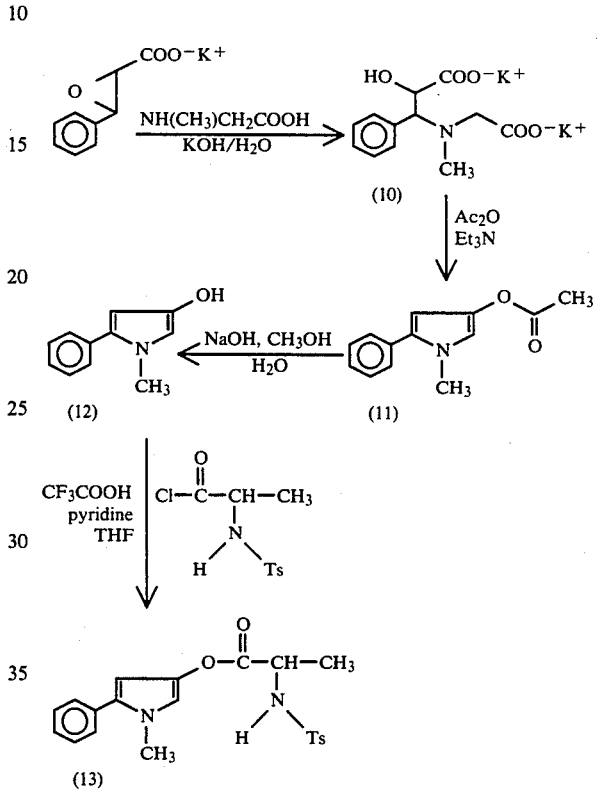

2-Hydroxy-3-(N-methylcarboxymethylamino)-hydrocinnamic acid dipotassium salt (10)

A mixture of β-phenylglycidic acid potassium salt (30 g; 0.15 mole), N-methylglycine (13.2 g; 0.15 mole), distilled water (119 ml) and KOH solution (9N; 22.3 ml) was heated to reflux for 3 hours to give a light yellow solution. The reaction mixture was evaporated to dryness under reduced pressure at 70° C. The residue was then crystallized from 95% EtOH (100 ml) to give a white solid which, after drying overnight under reduced pressure at 110° C., yielded 30.8 g of white solid (10) (yield 63%).

IR (KCl) cm$^{-1}$ 3360 (br), 1580, 1405, 705; $^1$H NMR (CD$_3$OD) δ2.30 (s, 3H), 2.98 (s, 2H), 3.70 (d, J=3 Hz, 1H), 4.48 (d, J=3 Hz, 1H), 4.92 (s, 1H), 7.40 (s, 5H); TLC Rf=0.51 (EtOH:1M triethylammonium bicarbonate, 7:3). (Product had no melting point less than 270° C.).

3-Acetoxy-1-methyl-5-phenylpyrrole (11)

A mixture of 2-hydroxy-3-(N-methylcarboxymethylamino)-hydrocinnamic acid dipotassium salt (10) (15.2 g, 46 mmole), acetic anhydride (173 ml) and triethylamine (308 ml) was heated at 90° C. for 19 hrs. The reaction mixture, which became deep brown in color, was filtered and the solid washed with ether. The filtrate was evaporated under reduced pressure to give a deep brown residue, which was taken up in ether (300 ml) and water (200 ml). The layers were separated and the ether layer washed with another portion of water (200 ml). The ether solution was then dried over MgSO₄, filtered and concentrated under reduced pressure to give 10.7 g of brown residue which was purified by evaporative distillation (120°–135° C.; 0.03 torr) and crystallization from ether to yield 3.0 g of white crystals (11) (yield 30%) mp=64°–65° C.

IR (CHCl₃) cm⁻¹ 2990, 1750, 1570, 1518, 1482, 1375, 1230 (br), 1024, 910, 700; ¹H NMR (CDCl₃) δ2.20 (s, 3H), 3.58 (s, 3H), 6.10 (d, J=2 Hz, 1H), 6.75 (d, J=2 Hz, 1H), 7.35 (s, 5H); TLC Rf=0.58 (hexane: EtOAc 7:3)

Anal. Calcd. for C₁₃H₁₃NO₂: C, 72.54; H, 6.10; N, 6.44; Found: C, 72.57; H, 6.09; N, 6.51.

3-(N-Tosyl-L-alaninyloxy)-1-methyl-5-phenylpyrrole (13)

To a mixture of deoxygenated methanol (15.5 ml) and 3-acetoxy-1-methyl-5-phenylpyrrole (11) (1.3 g, 6.2 mmole), under argon, was added deoxygenated NaOH (2N, 12.5 ml). The reaction mixture was stirred in an ice-bath for 15 minutes. Then deoxygenated citric acid (2M, 7 ml) was added and the resulting mixture was stirred in an ice bath for 8 minutes. The reaction mixture was concentrated under reduced pressure, then 20 ml of water was added and was extracted twice with ethylacetate (EtOAc) (50 ml). The EtOAc layers were combined, dried ovr MgSO₄, filtered and concentrated under reduced pressure to give 3-hydroxy-1-methyl-5-phenylpyrrole (12) as an orange residue. Under argon, a cold solution of anhydrous THF (12.4 ml), pyridine (0.6 ml, 7.4 mmole, 1.2 eq) and trifluoroacetic acid (1.2 ml, 15 mmole, 2.4 eq) was added to the orange residue, followed immediately by the addition of a solution of freshly prepared N-tosyl-L-alaninyl chloride (1.2 g, 7.4 mmole, 1.2 eq) in anhydrous THF (12.4 ml). The resulting mixture was stirred for one hr at 0° C. Then the reaction was quenched by the addition of aqueous citric acid (1M, 5 ml) and EtOAc (30 ml). After a brief mixing, the layers were separated and the organic layer was successively washed with saturated NaCl solution, twice with 5% NaHCO₃ solution and again with saturated NaCl solution. The EtOAc extract was then dried over MgSO₄, treated with Norit 211, filtered and concentrated under reduced pressure to give the crude product (13) as an orange residue. This was dissolved in hexane:EtOAc (1:1) (5 ml) and chromatographed on a column (SiO₂, 100 g) by elution with hexane:EtOAc (7:3) to give 1 g of (13) as a thick light orange oil. A portion of this crude product was further purified by semi-preparative HPLC (column, IBM silica, 1 cm×25 cm; mobile phase, hexane:EtOAc 8:2; flow rate, 4.0 ml/min; pressure, 0.2 psi) to yield a honey color thick oil (13).

IR (film) cm⁻¹ 3260, 2950, 1760, 1520, 1350, 1170, 770; ¹H NMR (DMSO-d₆) δ1.28 (d, J=7 Hz, 3H), 2.36 (s, 3H), 3.58 (s, 3H), 5.85 (d, J=2 Hz, 1H), 6.15 (m, 1H), 6.74 (d, J=2 Hz, 1H), 7.30–7.80 (m, 9H), 8.37 (d, J=8 Hz, 1H); ¹³C NMR (DMSO-d₆) δ18.205, 20.936, 34.917, 51.240, 100.598, 113.148, 126.544, 127.000, 128.105, 128.560, 129.601, 130.901, 132.202, 135.714, 138.315, 142.672, 169.724; TLC Rf=0.52 (toluene:dioxane 4:1); High-resolution mass spectrum, C₂₁H₂₂N₂O₄S requires m/e 398.1300, found m/e 398.1297.

7.2.4 Synthesis of 3-(N-tosyl-L-alaninyloxy)-5-(p-chlorophenyl)pyrrole (18)

A series of experiments was conducted to prepare the captioned ester compound corresponding to compound (I) in which A is N-tosyl-L-alaninyl, R is p-chlorophenyl, R* is H, X is NR' and R' Is H. The reaction sequence is as follows:

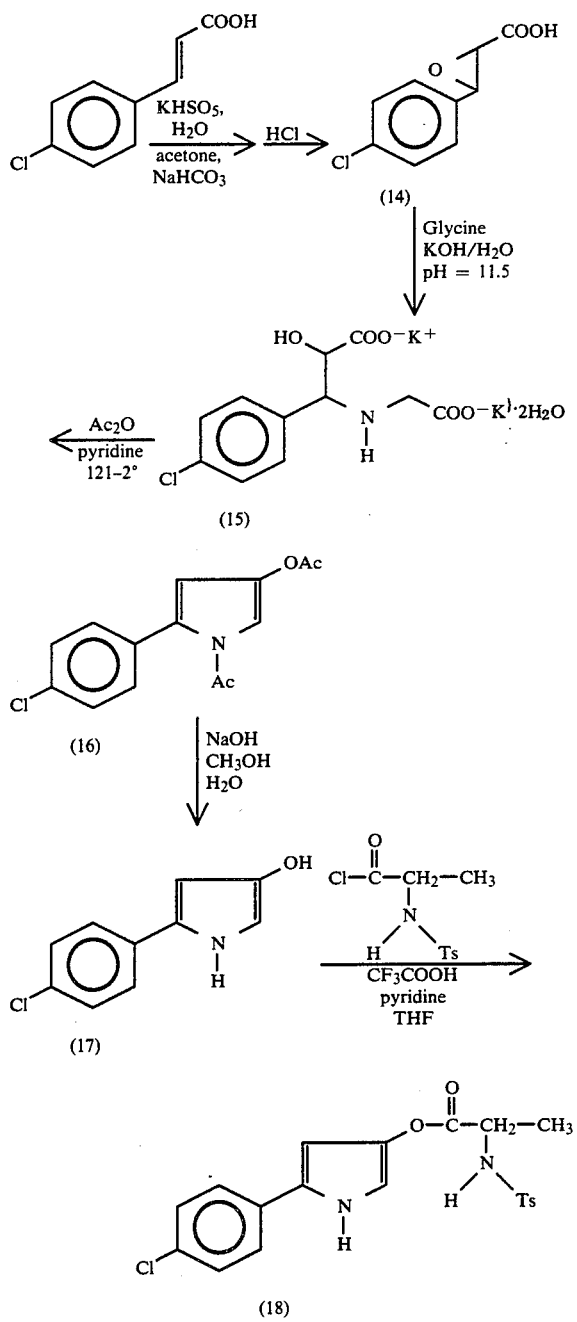

trans-β-(p-Chlorophenyl)glycidic acid (14)

To a stirred slurry of p-chlorocinnamic acid (68.5 g; 0.375 mol) in 260 mL of acetone was added NaHCO₃ (137 g; 1.63 mol), followed by slow addition of 260 mL of water. To this mixture was added, over 2.5 hours at 22°–27° C., a mixture of OXONE ® (211 g; 0.343 mol), 120 mg of disodium EDTA and 805 mL of water. After five hours the mixture was acidified with 70 mL of cold 12N HCl, to bring the pH down to about 2.5, and it then was extracted with 700 mL of ethyl acetate. The extract was washed with brine, dried with MgSO$_4$, filtered, and the filtrate was evaporated to dryness under vacuum. The white solids were crystallized from ethyl acetate: mp 121°-5° C. (72.2 g; 97% yield). $^1$H NMR (CDCl$_3$/DMSO-D$_6$) $\delta$7.3 (m, 4H), 4.05 (d, J=2, 1H), and 3.4 (d, J=2, 1H).

Anal. Calcd. for C$_9$H$_7$ClO$_3$: C, 54.43; H, 3.55; Cl, 17.85; Found: C, 54.53; H, 3.80; Cl, 17.91.

2-Hydroxy-3-(carboxymethylamino)-p-chlorohydrocinnamic acid dipotassium salt dihydrate (15)

To a solution of KOH (85%), (46.7 g; 0.709 mol) and 400 mL of water was added glycine (25.9 g; 0.345 mol) followed by trans-β-p-chlorophenylglycidic acid (14) (72.2 g; 0.3635 mol). This mixture was heated at 100° C. for two hours, cooled to room temperature and sufficient KOH added to raise the pH to 12. The turbid solution was extracted three times with ethyl acetate, which extract was then discarded; the clear aqueous solution (about 500 mL) was evaporated under vacuum to dryness using a 70° water bath. The solids were than dissolved in about 350 mL of hot ethanol, filtered, and the filtrate chilled in an ice bath for several hours. The crystallized solids were collected by filtration and washed with some cold ethanol: mp 93°-5° C. with decarboxylation at 185° C. (57.2 g; 41%).

$^1$H NMR (D$_2$O-TSP) $\delta$7.4 (s, 4H), 4.7 (s, 6H, exchangable protons), 4.4 (d, J=4, 1H), 4.05 (d, J=4, 1H), and 3.1 (s, 2H).

Anal. Calcd. for C$_{11}$H$_{10}$ClNO$_5$K$_2$.2H$_2$O: C, 34.24; H, 3.66; N, 3.63; Found: C, 34.40; H, 4.03; N, 3.42.

N-acetyl-3-acetoxy-5-(p-chlorophenyl)pyrrole (16)

To the 2-hydroxy-3-(carboxymethylamino)-p-chlorohydrocinnamic acid dipotassium salt dihydrate (15) (10 g; 0.02591 mol) was added acetic anhydride (40 mL) and pyridine (30 mL). This mixture was gently heated to 35° C. at which point the solution exothermed to 67° then began to fall, whereupon heating was again resumed. The mixture was heated at 121°-2° (internal temperature) for one hour then cooled. To the reaction mixture was added about 30 mL of ethyl acetate which precipitated most the pyridinium acetate salt; this salt was collected by filtration and washed with a small amount of ethyl acetate. The filtrate was then evaporated under vacuum to an oil and ice water added. The product was extracted with ether and the ether extracts were successively washed twice with cold dilute aq. citric acid, cold water, three times with cold dilute aq. NaHCO$_3$, cold water and brine, followed by drying over MgSO$_4$ and filtering. The filtrate was treated with 10 g of Darco, stirred for 20 minutes and then filtered. The filtrate was evaporated under vacuum to an oil. To the oil was added 25 mL of 2-propanol. The resultant solution yielded, with chilling and scratching, pale yellow crystals; mp 69°-71° C. (3.4 g; 47%); TLC Rf=0.61 (toluene:dioxane, 95:5). An analytical sample was recrystallized from 2-propanol, but no change in mp was observed.

IR (KCl) cm$^{-1}$ 1755 (C=O, ester) and 1730 (C=O, amide); $^1$H NMR (CDCl$_3$) $\delta$7.4 (m, 5H), 6.2 (d, J=2, 1H), 2.4 (s, 3H) and 2.3 (s, 3H).

Anal. Calcd. for C$_{14}$H$_{12}$ClNO$_3$: C, 60.55; H, 4.36; H, 5.04; Found: C, 60.65; H, 4.55; N, 5.07.

3-hydroxy-5-(p-chlorophenyl)pyrrole (17)

A sample of N-acetyl-3-acetoxy-5-p-chlorophenylpyrrole (16) (2.8 g; 0.01 mol) was deoxygenated for ten minutes with a stream of N$_2$. The solids were then dissolved in deoxygenated methanol (30 mL) which was then chilled to −8° C. At once was added a cold deoxygenated solution of NaOH (1.6 g; 0.04 mol) in 20 mL H$_2$O, which solution was then heated briefly to 15° C. and then immediately cooled to −5° C.; after 25 minutes the clear solution was treated with a cold deoxygenated solution of citric acid (4.2 g; 0.02 mol) in 15 mL H$_2$O and the temperature rose briefly to 5° C. After 0.5 hour of stirring at −5° C. the solids were collected by filtration and washed with cold deoxygenated H$_2$O. The pale green product was dried under vacuum at room temperature over P$_2$O$_5$ for several days (1.3 g; 68%); TLC Rf=0.19 (CHCl$_3$:EtOH, 9:1); IR (KCl) showed no evidence for C=O absorption.

Anal. Calcd. for C$_{10}$H$_8$ClNO.1/6H$_2$O: C, 61.08; H, 4.27; N, 7.12; Found: C, 61.36; H, 4.44; N, 6.85.

3-(N-tosyl-L-alaninyloxy)-5-(p-chlorophenyl)pyrrole (18)

To N$_2$ deoxygenated THF (15 mL) was added pyridine (0.65 mL; 0.008 mol), trifluroracetic acid (1.27 mL; 0.0164 mol), and 3-hydroxy-5-p-chlorophenylpyrrole (17) (1.3 g; 0.0065 mol). The solution was chilled to 0° C. to −4° C. and a N$_2$ deoxygenated, chilled (0° C. to −4° C.) solution of N-tosyl-L-alaninyl chloride (2.1 g; 0.008 mol) in 15 mL of THF was added over 10 minutes. After maintaining the mixture at 0° C. for one hour, a mixture of ice and 100 mL of 1N citric acid was added. This mixture was extracted with ethyl acetate and the extract washed once with cold brine, twice with cold dilute NaHCO$_3$, and once with cold brine, following which, it was dried over MgSO$_4$ and filtered. The filtrate was treated with 2 g of Darco and stirred for ten minutes, filtered and the filtrate concentrated under vacuum to a reddish-brown oil. A second treatment with 1.3 g Darco afforded a light reddish oil. The oil was dissolved in toluene:cyclohexane (4:1) and placed in the refrigerator overnight. Light salmon crystals were obtained. (1.45 g; 53%); mp 113°-5° C.; TLC Rf=0.47 (Et$_2$O); IR (KCl) cm$^{-1}$ 1740 (C=O, ester); $^1$H NMR (CDCl$_3$) $\delta$8.4 (br s, 1H), 7.8-7.2 (m, 8H), 6.7 (m, 1H), 6.2 (m, 1H), 5.5 (d, J=9, 1H), 4.2 (p, J=8, 1H), 2.4 (s, 3H), 1.4 (d, 3H); MS (EI, DIP) m/e 418 (M+, 2.3%) and 420 (M+, 0.8%).

Anal. Calcd. for C$_{20}$H$_{19}$ClN$_2$O$_4$S: C, 57.34; H, 4.57; N, 6.69; Found: C, 57.53; H, 4.58; N, 6.67.

7.3 Preparation and Use of Various Test Devices

A series of Experiments was conducted to prepare test devices of the present invention in which the ester substrates of paragraph 7.1, supra, were tested for responsiveness to leukocytes in urine. The devices comprised a small square of filter paper containing the assay reagents, the paper mounted at one end of a polystyrene film strip. The filter paper was impregnated with buffer, the ester an accelerator and a diazonium salt coupling agent. Each of the devices tested was found to exhibit a positive test for leukocytes in urine.

7.3.1 Test device in which the ester is 3-(N-tosyl-L-alaninyloxy)-5-phenylpyrrole (4)

A test device, sensitive to the presence of leukocytes in urine, was prepared. The device comprised a small square of filter paper mounted at one end of an oblong strip of polystyrene film. The paper was impregnated with various ingredients including a chromogenic ester, an accelerator and a diazonium salt. A 2 inch wide strip of Eaton and Dickman #205 filter paper was immersed in an aqueous solution containing the following:

0.4M borate-NaOH buffer pH=8.6
2.0% (w/v) polyvinylpyrrolidone K-30
0.2% (w/v) Bioterge AS-40 ®
0.25M NaCl The paper was then dried for 7 minutes in an Overly Air Foil paper dryer at 175°–200° F. at an airflow pressure of 1 inch of $H_2O$. Next, the dried paper was immersed in an acetone solution containing 2.0% (v/v) n-decanol
0.75 mM 2-methoxy-4-morpholinobenzene diazonium chloride
0.5 mM 3-(N-tosyl-L-alaninyloxy)-5-phenylpyrrole Following this impregnation the paper was dried for 10 minutes in a ventilated Hotpack ® oven at 130° F. An off-white test paper was obtained.

A piece of the dried, impregnated paper was cut to a square measuring 0.2 inches on a side and mounted at one end of an axially oriented polystyrene strip measuring 4 inches by 0.2 inches. Mounting the paper to the strip was achieved using Double Stick double faced adhesive (3M Company).

7.3.2 Test device in which the ester is 3-(N-tosyl-L-alaninyloxy)-5-phenylthiophene (9)

A test device sensitive to the presence of leukocytes in urine was prepared, wherein 3-(N-tosyl-L-alaninyloxy)-5-phenylthiophene was used as the indicator. A piece of filter paper (Eaton & Dikeman #205) was immersed in an aqueous first solution containing the following:

0.4M borate-NaOH buffer (pH=8.5)
0.4M NaCl
1.5% (w/v) polyvinylpyrrolidone (K-30)

The impregnated paper was dried in a forced air oven for 30 minutes at 70° C., whereupon it was permitted to cool to room temperature and impregnated with a second dip solution comprising an acetone solution containing:

0.75 mM 3(-N-tosyl-L-alaninyloxy)-5-phenylthiophene
0.75 mM 2-methoxy-4-morpholinobenzene diazonium chloride, zinc chloride double salt
0.5% (v/v) n-decanol The doubly impregnated paper was then dried in a forced air oven for 5 minutes at 50° C.

The dried paper was cut into squares measuring 0.2 inches on a side and mounted at the end of a polystyrene film measuring 0.2 by 3.25 inches. Mounting was accomplished using Double Stick, a double faced adhesive from 3M Company. The test device was stored in bottles of 100 each, together with silica gel and molecular sieves to provide dessication.

7.3.3 Test device in which the ester is 3-(N-tosyl-L-alaninyloxy)-1-methyl-5-phenylpyrrole (13)

Test devices were prepared following the procedure in experiment 7.3.2 in which the ester indicator was 3-(N-tosyl-L-alaninyloxy)-1-methyl-5-phenylpyrrole and the coupling agent was 1-diazonaphthalene-4-sulfonate. The aqueous first dip solution contained:

0.4M boric acid
2.0% (w/v) polyvinylpyrrolidone (K-30)
0.2% (v/v) Bioterge AS-40
0.25M NaCl Prior to impregnation of the filter paper, the solution was titrated with NaOH to a pH of 9.0.

The second dip solution in acetone contained:
0.75 mM 1-diazonaphthalene-2-sulfonate
1.3 mM 1-methyl-3-(N-tosyl-L-alaninyloxy)-5-phenylpyrrole
1.5% (v/v) dodecanol Following impregnation in the aqueous first dip, the paper was dried for about 5 minutes at about 80° C., and for about 5 minutes at 70° C. following impregnation in the acetonic second dip.

The dried paper was mounted as in experiment 7.2.2.

7.3.4 Test device in which the ester is 3-(N-tosyl-L-alaninyloxy)-5-(p-chlorophenyl)pyrrole (18)

Test devices were prepared as in Experiment 7.3.3 except that the acetone solution contained, in place of the phenylpyrrole, 1.3 mM 3-(N-tosyl-L-alaninyloxy)-5-(p-chlorophenyl)pyrrole.

7.4 Evaluation of the Test Device

The test devices prepared in the experiments of paragraph 7.3 were subjected to evaluation of their ability to detect leukocytes present in urine.

Test samples were prepared from a normal human urine pool. One sample served as a blank and leukocytes isolated from freshly drawn blood were added to two additional urine samples to yield concentrations of 0, 10 and 75 leukocytes/$\mu$L, respectively.

Test devices were quickly immersed in and removed from a test sample. Two minutes later the devices were observed using a spectrophotometer to measure %reflectance at different wavelengths from 400–700 nm (nanometers).

The data show that all of the test devices demonstrated clearly discernable differences in light reflectance corresponding to different leukoctye levels in the test samples. The data are presented in the following table:

| Experiment No. | Leukocyte Concentration (cells/$\mu$L) | % Reflectance at 555 nm |
| --- | --- | --- |
| 7.3.1* | 0 | — |
|  | 10–12 | — |
| 7.3.2 | 0 | 65 |
|  | 10 | 60 |
|  | 65 | 42 |
| 7.3.3 | 0 | 67 |
|  | 10 | 64 |
|  | 75 | 60 |
| 7.3.4 | 0 | 61 |
|  | 10 | 51 |
|  | 75 | 42 |

*Visual observation: purple color formed at 10–12 cells/$\mu$L; blank gave no color change

What is claimed is:

1. A composition for determining the presence of leukocytes, esterase or protease in a test sample, the composition comprising
   an ester having the structure

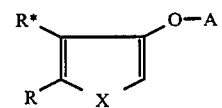

in which:

A is an N-blocked-$\alpha$-L-amino acid residue or an N-blocked-$\alpha$-L-peptide acid residue, X is O, S, or NR', R is aryl, or lower alkyl group having 1 to 6 carbon atoms, R* is H, or lower alkyl group having 1 to 6 carbon atoms, and R' is H, lower alkyl group having 1 to 6 carbon atoms or aryl; and a suitable buffer substance which when in contact with an aqueous test sample will provide a resultant pH of at least about 7.

2. The composition of claim 1 in which X is NR'.

3. The composition of claim 1 in which A is an N-blocked amino acid.

4. The composition of claim 1 in which A is N-blocked-L-alaninate.

5. The composition of claim 1 in which A is N-blocked-L-alaninate, R is phenyl, X is NR', and both R' and R* are H.

6. The composition of any one of claims 1–5 in which the composition further comprises an accelerator.

7. The composition of claim 6 in which the accelerator is an alcohol having 1–15 carbon atoms.

8. The composition of any one of claims 1–5 in which the composition further comprises a diazonium salt coupling agent.

9. The composition of claim 8 in which said diazonium salt is a zwitterion having the structure

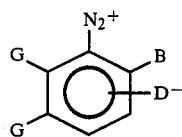

in which
D⁻ is an anion,
G, same or different, is H, lower alkyl group having 1 to 6 carbon atoms, or aryl, or
in which both G together form a fused ring system, and
in which B is H or OH.

10. The composition of claim 8 in which said salt is 1-diazo-2-naphthol-4-sulfonate.

11. The composition of any one of claims 1–5 in which the composition further comprises an accelerator and a diazonium salt coupling agent.

12. The composition of claim 11 in which the accelerator is an alcohol having 1–15 carbon atoms.

13. The composition of claim 11 in which the accelerator is an alcohol having from about 8 to 15 carbon atoms, and the diazonium salt is 1-diazo-2 naphthol-4-sulfonate.

14. A test device for determining the presence of leukocytes, esterase or protease in a test sample, the device comprising a carrier matrix incorporated with an ester having the structure

in which:
A is N-blocked-α-L-amino acid residue or N-blocked-α-L-peptide residue,
R is aryl or lower alkyl group having 1 to 6 carbon atoms,
X is O, S, or NR',
R' is H, lower alkyl group having 1 to 6 carbon atoms or aryl and R* is H, or lower alkyl group having 1 to 6 carbon atoms; and a suitable buffer substance which when in contact with an aqueous test sample will provide a resultant pH of at least about 7.

15. The test device of claim 14 in which X is NR'.

16. The test device of claim 14 in which A is N-blocked amino acid residue.

17. The test device of claim 14 in which A is N-blocked-L-alaninate.

18. The test device of claim 14 in which A is N-blocked-L-alaninate, R is phenyl, X is RN', and both R* and R' are H.

19. A method for determining the presence of leukocytes, esterase or protease in a test sample, the method comprising contacting the sample with the test device of any one of claims 14–18, and observing a detectable response.

20. The test device of any one of claims 14–18 wherein the carrier matrix is additionally incorporated with an accelerator.

21. The test device of claim 20 in which the accelerator is an alcohol having 8–15 carbon atoms.

22. A method for determining the presence of leukocytes, esterase or protease in a test sample, the method comprising contacting the sample with the test device of claim 20 and observing a detectable response.

23. The test device of claim 20 in which the accelerator is an alcohol having 1–15 carbon atoms.

24. A method for determining the presence of leukocytes, esterase or protease in a test sample, the method comprising contacting the sample with the test device of claim 23 and observing a detectable response.

25. The test device of any one of claims 14–18 wherein the carrier matrix is additionally incorporated with a diazonium salt coupling agent.

26. A method for determining the presence of leukocytes, esterase or protease in a test sample, the method comprising contacting the sample with the test device of claim 25 and observing a detectable response.

27. The test device of claim 24 in which the salt is 1-diazo-2-naphthol-4-sulfonate.

28. The test device of claim 22 in which the diazonium salt is a zwitterion having the structure in which:
B is H or OH;
D is an anion;
G, same or different, is H, lower alkyl group having 1 to 6 carbon atoms, or aryl, or
in which both G together form a fused ring structure.

29. The test device of claim 28 in which the carrier matrix is additionally incorporated with an accelerator.

30. The test device of claim 29 in which the accelerator is an alcohol having 1–15 carbon atoms.

31. A method for determining the presence of leukocytes, esterase or protease in a test sample, the method comprising contacting the sample with the test device of claim 26, 30, and observing a detectable response.

32. The test device of claim 29 in which the accelerator is an alcohol having 8–15 carbon atoms.

33. A method for determining the presence of leukocytes, esterase or protease in a test sample, the method comprising contacting the sample with the test device of claim 32 and observing a detectable response.

* * * * *